US006475534B2

(12) United States Patent
Xie et al.

(10) Patent No.: US 6,475,534 B2
(45) Date of Patent: *Nov. 5, 2002

(54) GINKGO BILOBA COMPOSITION, METHOD TO PREPARE THE SAME AND USES THEREOF

(75) Inventors: De Long Xie, Shanghai (CN); Ning Wang, Shanghai (CN); Qi Gao, Shanghai (CN); Guo An Zhang, Shanghai (CN); Bao Ping Shao, Shanghai (CN); Xiao Wu Jin, Shanghai (CN); Xin Sheng Huang, Shanghai (CN)

(73) Assignee: Shanghai Xingling Sci. & Tech. Pharmaceutical Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 09/768,678

(22) Filed: Jan. 24, 2001

(65) Prior Publication Data

US 2001/0055629 A1 Dec. 27, 2001

Related U.S. Application Data

(63) Continuation of application No. 09/097,058, filed on Jun. 12, 1998, now Pat. No. 6,187,314, which is a continuation of application No. 09/044,551, filed on Mar. 19, 1998, now Pat. No. 6,030,621.

(51) Int. Cl.$^7$ ............................................. A61K 35/78
(52) U.S. Cl. ...................................... 424/752
(58) Field of Search ......................... 424/752

(56) References Cited

U.S. PATENT DOCUMENTS

| | | | |
|---|---|---|---|
| 4,981,688 A | | 1/1991 | Ayroles et al. |
| 5,002,965 A | | 3/1991 | Ramwell et al. |
| 5,089,636 A | | 2/1992 | Kwak et al. |
| 5,098,709 A | | 3/1992 | Kang et al. |
| 5,128,131 A | | 7/1992 | Motoyama et al. |
| 5,158,770 A | | 10/1992 | Saito et al. |
| 5,194,259 A | | 3/1993 | Soudant et al. |
| 5,241,084 A | | 8/1993 | Teng et al. |
| 5,322,688 A | | 6/1994 | Schwabe et al. |
| 5,389,370 A | | 2/1995 | O'Reilly et al. |
| 5,399,348 A | | 3/1995 | Schwabe et al. |
| 5,466,829 A | | 11/1995 | Park et al. |
| 5,512,286 A | | 4/1996 | Schwabe et al. |
| 5,541,183 A | | 7/1996 | Park et al. |
| 5,599,950 A | | 2/1997 | Teng et al. |
| 5,637,307 A | * | 6/1997 | Bombardelli |
| 6,030,621 A | | 2/2000 | De Long et al. |
| 6,221,356 B1 | * | 4/2001 | Junsheng |
| 6,174,531 B1 | | 1/2002 | Zhang et al. |

FOREIGN PATENT DOCUMENTS

| | | |
|---|---|---|
| CN | 1145230 | 3/1997 |
| JP | 2-73079 | 3/1990 |
| JP | 2-121998 | 5/1990 |
| JP | 3-24084 | 2/1991 |
| JP | 3-98592 | 4/1991 |
| JP | 3-227985 | 10/1991 |
| JP | 3-264533 | 11/1991 |
| JP | 3-275629 | 12/1991 |
| JP | 4-182434 | 6/1992 |

OTHER PUBLICATIONS

DeFeudis, F. V. Clinical Studies and Clinical Pharmacology with Egb 761, ibid. pp. 97–125.

DeFeudis, F. V. In Vitro Studies with EGb 761, in Ginkgo biloba Extract (Egb761): Pharmacological Activities and Clinical Applications, F. V. DeFeudis, Elsevier, Paris 1991, pp. 25–60.

DeFeudis, F. V. In Vivo Studies with EGb 761, in Ginkgo biloba Extract (EGb 761): Pharmacological Activities and Clinical Applications, F. V. DeFeudis, Elsevier, Paris 1991, pp. 61–78.

DeFeudis, F. V. Machanisms and Concepts of Action of Egb 761: Theoretical Considerations, ibid. pp. 147–152.

DeFeudis, F. V. Safty of Egb 761–Containing Products, ibid, pp. 143–146.

Pietri,S.et al, Effect of Ginkgo biloba extract (Egb 761) on tree radical–induced ischemia–repertusion injury in isolated rat hearts: a hemodynamic and electron–spin–resonance investigation, in advances in Ginkgo biloba Extract Research, vol. 2, Ginkgo biloba Extract (Egb 761) as a Free–Radical Scavenger, C. Ferradini et al. eds, Elsevier, Paris 1993, pp. 163–171.

Spinnewyn, B. et al, Effect of Ginkgo biloba extract (Egb 761) on oxygen consumption by isolated cerebral mitochondria, in Advances in Ginkgo biloba Extract Research, vol. 4. Effects of Ginkgo biloba Extract (Egb 761) on Aging and age–Related Disorders, Y. Christen et al. eds, Elsevier, Paris, 1995, pp. 17–22.

Xie, De Long et al. Ginkgo Biloba Composition, Method to Prepare the Same and Uses Thereof U.S. Ser. No.: 09/097, 058; Filing Date Jun. 12, 1998 claiming for priority of U.S. Ser. No.: 09/044,551 filed on Mar. 19, 1998, now U.S. patent 6,030,621 issued on Feb. 29, 2000.

\* cited by examiner

*Primary Examiner*—Christopher R. Tate
(74) *Attorney, Agent, or Firm*—Albert Wai Kit Chan; Mark Elkins

(57) ABSTRACT

This invention provides different compositions extracted from Ginkgo biloba leaves. Said compositions comprise new active components. This invention also provides a method of preparation of the compositions and individual components of said compositions. Finally, this invention provides various uses of this composition.

4 Claims, No Drawings

GINKGO BILOBA COMPOSITION, METHOD TO PREPARE THE SAME AND USES THEREOF

This application is a continuation application of U.S. Ser. No. 09/097,058, filed Jun. 12, 1998 now U.S. Pat. No. 6,187,314 continuation application of U.S. Ser. No. 09/044,551, filed Mar. 19, 1998, now U.S. Pat. No. 6,030,621, issued on Feb. 29, 2000, the content of the preceeding applications is hereby incorporated by reference into this application.

Throughout this application, various publications are referenced and full citations for these publications may be found in the text where they are referenced. The disclosures of these publications are hereby incorporated by reference into this application in order to more fully describe the state of the art as known to the skilled therein as of the date of the invention described and claimed herein.

BACKGROUND OF THE INVENTION

Ginkgo Biloba is the oldest genus among existing seed plants and the only survivor of the family Ginkgoaceae, that can be traced back more than 200 million years to the fossils of the Permian period. Preparations of Ginkgo Biloba leaves have been used as remedies in China for more than 5,000 years, I. e. since the earliest origin of Chinese herbal medicine. Phytopharmaceutical extracts from the leaves of Ginkgo biloba have been applied to treat cerebrovascular and peripheral vascular diseases in many countries, such as Germany, France, Japan and Korea since the 1960's.

The principal effective component in Ginkgo biloba leaves is flavonoids, that comprise at least 14 different compounds, such as flavonols, flavones, flavanols and biflavonoids etc. Among all these compounds, flavone glycosides and flavonol glycosides, that include kaempferol, quercetin and isorhamnetin with glucose or rhamnose, are the most emphasized in Ginkgo biloba extracts on the market for therapeutic purposes (Tebonin®, Tanakan®, Roekan®, or "EGb 761"). As experiments have demonstrated, flavone glycosides and flavonol glycosides are potent antioxidants that scavenge oxygen free radicals, thereby preventing age-related cell and tissue damage that can adversely affect various mental functions, including memory and concentration; see J. Pincemail et al., La Presse Medicale Vol. 15 (1986), 1475–1479; J. Robak et al., Biochem Pharmacol Vol 37 (1988), 837–841 and J. Kleijnen and P. Knipschild, Ginkgo biloba (Drug Profiles), the Lancet 340:1136 (1992). In addition, the flavone glycosides and flavonol glycosides increase peripheral circulation. Methods of preparation of Ginkgo biloba extracts with a greatly enriched content of flavone glycosides as the active components are described in DE-B 17 67 098 and DE-B 21 17 429. These preparations are Ginkgo biloba monoextracts.

Besides flavonoids, another major active constituent in Ginkgo biloba leaves is terpene lactones, that include ginkgolides A, B, C, J, M and bilobalide. Ginkgolides are terpenoid substances with lactone structure; see K. Nakanishi, Pure and Applied Chemistry, Vol. 14 (1967), 89-113; M. Maruyama et al., Tetrahedron Letters (1967), 299–302 and 303–319 and K. Okabe et al., Ginkgolides, j. Chem. Soc. (1967), 2201–2206. They are twenty carbon cage molecules, incorporating a t-butyl group and six 5-membered rings A to F including a spiro [4.4] nonane, a tetrahydrofuran cycle and three lactone rings. The various ginkgolide structures differ only by the number and position of hydroxyl groups on the C1, C3 or C7 of the spirononane framework. Recently, it has been found that, by their property of inhibiting platelet activating factor (PAF), Ginkgolides A, B, C and M, especially ginkgolide B are effective in treating platelet activating factor acether-induced diseases such as asthma, bronchitis, dementia senilis, allergy, cardiac disorders, rheumatic diseases, etc. and a broad range of other circulatory system diseases; see U.S. Pat. No. 4,734,280; P. Braquet, Drug of the Future, 12, 643, 1987; V. Lamant et al., Biochem Pharmacol Vol. 36 (1987) 2749–52; K. Becker et al., Biomed Biochim Acta Vol. 47 (1988) 10–11; P. Braquet et al., J Ethnopharmacol Vol. 32 (1991) 135–9 and B. Steinke et al., Planta Med Vol. 59 (1993) 155–60. Ginkgolides A and B also have cerebroprotective property by increasing cerebral blood flow; see J. Krieglstein et al., European Journal of Pharmaceutical Sciences Vol. 3 (1995) 39–48. U.S. Pat. No. 5,002,965 describes a method of using ginkgolides to prevent reperfusion injury in organ transplantation.

DE-A 33 38 995 and the corresponding U.S. Pat. No. 4,571,407 disclose using bilobalide, a sesquiterpene lactone structurally related to ginkgolides (see K. Nakanishi et al., R. T. Major et al. and K. Weinges et al., J. Am. Chem. Soc., Vol. 93, 1971, 3544–3546) to treat encephalopathies, cerebral edemas, demyelinating neuropathies and myelopathies. When bilobalide was administered to the infarct area prior to occlusion to the middle cerebral artery, the cortical and infarct volume decreased substantially; see J. Krieglstein et al., European Journal of Pharmaceutical Sciences Vol. 3 (1995) 39–48. Experiments have also demonstrated that bilobalide can help restore the motor nerves in animals; see C. Bruno et al., Planta Med 59, 1993, 302–307. In addition, in vitro and in vivo tests have proved that bilobalide has the property to inhibit Pneumocystis carinii growth; see C. Atzori et al., Antimicrobe Agents Chemother 37(7), 1993, 1492–1496. U.S. Pat. No. 5,264,216 discloses a method of using bilobalide to treat an infection with a pathological strain selected from the group consisting of *Trichomonas vaginalis, Staphylococcus aureus, Streptococcus faecalis, Escherichia coli,* Lactobacillus sp. and *Pneumocystis carinii.* Activity of bilobalide against infection with Pneumocystis carinii has major utility in treating AIDS-associated infections.

In addition to the compounds mentioned above, Ginkgo biloba leaves also contain at least 12 alkyl phenolic acid compounds including ginkgolic acids (anacardic acids) that are 6-alkylsalicylic acids with n-C13- to n-C19-alkyl groups with 0 to 3 double bonds; see J. L. Gellermann et al., Phytochemistry, Vol. 15 (1976), 1959–1961 and Analytic. Chem., Vol. 40 (1968), 739–743. Structurally similar to the irritants in poison ivy, ginkgolic acids are the factors responsible for toxic effects of Ginkgo biloba extracts, that include gastrointestinal disturbances, headaches, skin irritation, dermatitis and edema. Many cases of allergic reactions after contact with Ginkgo biloba leaves or fruits have been reported since the 1960's; see G. A. Hill et al., J. Am. Chem. Soc., Vol. 56 (1934), 2736–2738; W. F. Sowers et al., Arch. Dermatol., Vol. 91 (1965), 452–456; L. E. Becker et al., J. Am. Med. Assoc., Vol. 231 (1975), 1162-1163; T. Nakamura, Contact Dermatitis, Vol. 12 (1985), 281-282; R. R. Tomb et al., Contact Dermatitis, Vol. 19 (1988) 281–3 and J. P. Lepoittevin et al., Arch Dermatol Res Vol. 281 (1989), 227–30. As a result, scientists in many countries have made notable efforts to develop substances and methods of desensitization against the allergies caused by ginkgolic acids (see U.S. Pat. No. 4,428,965). DE-B 17 67 098 and DE-B 21 17 429 developed a process to remove alkylphenol compounds with a chlorinated aliphatic hydrocarbons such as carbon tetrachloride. However the therapeutically valuable ginkgolides and the bilobalide are also considerably reduced in this process. DE-B 21 17 429 also adopted a technology to eliminate the polyphenol compounds with tanning properties (proanthocyanidins) in which lead compounds are applied. Problems with these processes are the health risks for the people involved, the potential danger to the environment and the possibility of undesirable residues in pharmaceutical.

Ginkgo biloba extract used most frequently at present for therapeutic purposes (Tebonin®, Tanakan®, Roekan®, or "EGb 76111") contains 24% flavone glycosides and 6% terpene lactones; see K. Drieu, La Presse Medicale Vol. 15 (1986), 1455–1457. These are the ginkgolides A, B, C and J as well as the bilobalide, which makes up approximately half of the 6%. Ginkgo biloba extract normally contains less than 10 ppm (parts per million) alkylphenol compounds. The therapeutic daily dosage is 120 mg.

Great efforts have been made in the 1990's to enrich the active therapeutic components of Ginkgo biloba extract and to reduce its content of ginkgolic acids. At the same time, possibilities have been exploited to provide specific combinations of the effective components of Ginkgo biloba extract for different therapies. A combination of the ginkgolide components and the flavone glycosides will shift the active profile of the extract towards the anti-PAF-effects. By contrast, a combination of the bilobalide and the flavone glycosides will apply the active profile more effectively against encephalopathies, cerebral edemas, demyelinating neuropathies and myelopathies. At the same time, methods have been developed for not using chlorinated aliphatic hydrocarbons to remove the alkylphenol compounds and not using lead compounds to remove proanthocyanidins.

U.S. Pat. No. 5,399,348 refers to a method for preparation of Ginkgo biloba extract in which the alkylphenol compounds are separated not by using chlorinated aliphatic hydrocarbon, but first through a process of precipitation and filtration, then through a multi step liquid-liquid-extraction with an aliphatic hydrocarbon. However, a lead compound or a polyamide is used to remove proanthocyanidins. The method is described as follows: Ginkgo biloba leaves are extracted with an organic solvent selected from the group consisting of aqueous acetone, an aqueous alkanol having one to three carbon atoms and anhydrous methanol. Most of the organic solvent is separated from the extract to form an aqueous solution, which is then diluted with water to a solids content of 5 to 25 weight percent. The diluted aqueous solution is then cooled to precipitate and lipophilic components are removed. The aqueous solution is next treated with ammonium sulfate and extracted with methylethylketone, acetone, or a mixture of methylethylketone and acetone. The extract is diluted with water and alcohol to form an aqueous alcohol solution, which is treated with a lead compound or an insoluble polyamide. The treated aqueous alcohol solution is last extracted with an aliphatic or cycloaliphatic solvent to further remove the alkylphenol compounds and a dry extract is recovered.

In addition, after being extracted with a solvent selected from the group consisting of methylethylketone or a mixture of methylethylketone and acetone, the extract can be concentrated to a solids content of 50 to 70% and the concentrate is then diluted with water and ethanol to form an aqueous alcohol solution containing about 50 weight percent of water and about 50 weight percent of ethanol with a solids content of about 10 weight percent. Next an aqueous solution of a lead salt, that is selected from the group consisting of lead acetate, lead hydroxide acetate or lead nitrate, or an aqueous suspension of lead hydroxide, preferably a solution of lead hydroxide acetate, is added to the above-mentioned aqueous alcohol solution until a change in color from brown to umber takes place and precipitate is formed and separated. The aqueous alcohol solution is next extracted with an aliphatic or cycloaliphatic solvent to further remove the alkylphenol compounds and then concentrated to a maximum ethanol content of about 5%. Next ammonium sulfate is added up to a content of 20 weight percent. The aqueous alcohol solution obtained is extracted with a mixture of methylethylketone and ethanol in a ratio of 9:1 to 4:6, to form an organic phase extract, which is concentrated to a solids content of 50 to 70 weight percent. The resultant concentrate is dried. Instead of a lead salt, a polyamide such as polyamide-6, polyamide-6.6 or cross-linked polyvinyl pyrrolidone (Polyvidon) can also be used.

U.S. Pat. No. 5,399,348 discloses that by applying the above-mentioned methods, a preparation from the leaves of Ginkgo biloba can be achieved with a content of 20 to 30% flavone glycosides, 2.5–4.5% ginkgolides A, B, C and J, 2.0–4.0% bilobalide, less than 10 ppm alkylphenol compounds and less than 10% proanthocyanidins.

U.S. Pat. No. 5,322,688 develops a similar process to remove the alkylphenol compounds, which is described above. But instead of using a lead compound to remove proanthocyanidins, U.S. Pat. No. 5,322,688 adopts a process of extraction with a water-immiscible alkanol of 4 or 5 C-atoms such as n-butanol. The method is characterized in that Ginkgo biloba leaves are extracted with an organic solvent selected from the group consisting of aqueous acetone, an aqueous alkanol having one to three carbon atoms and anhydrous methanol. Most of the organic solvent is then separated from the extract by evaporation or distillation to form an aqueous solution, which is diluted with water to a solids content of 5 to 25 weight percent. The diluted aqueous solution is cooled to precipitate and remove the water-insoluble lipophilic components. Then the aqueous solution is treated with 10–30% ammonium sulfate and extracted with a solvent selected from the group consisting of methylethylketone and a mixture of methylethylketone and acetone. The extract is extracted next with butanol or pentanol and the butanol or pentanol extract is diluted with water and alcohol to form an aqueous alcohol solution, which is then extracted with an aliphatic or cycloaliphatic solvent to further remove the alkylphenol compounds. Finally the aqueous extract solution is concentrated and the resultant concentrate is dried to form a dry extract.

In addition, after being extracted with a solvent selected from the group consisting of methylethylketone and a mixture of methylethylketone and acetone, that is described above, the extract can also be concentrated to a solids content of 50 to 70% and then diluted with water to a solids content of about 10 weight percent. The aqueous concentrate is next extracted with water-immiscible C4 or C5 alkanol to form alkanol layers, that are concentrated to a solids content of 50 to 70 weight percent. The concentrate is then diluted with water and ethanol to form a solution having 5 to 20 weight percent dry extract in 20 to 60 weight percent aqueous ethanol, which is further extracted with an aliphatic or cycloaliphatic solvent to further remove alkylphenol compounds. Finally the aqueous extract solution is concentrated and the resultant concentrate is dried to form a dry extract.

U.S. Pat. No. 5,322,688 reveals that by applying the above-mentioned method, a preparation from the leaves of Ginkgo biloba can be achieved with a content containing 20 to 30 weight percent flavone glycosides, 2.5 to 4.5 weight percent of ginkgolides A, B, C and J, 2.0 to 4.0 weight percent bilobalide, less than 10 ppm alkylphenol compounds and less than 10 weight percent proanthocyanidins.

U.S. Pat. No. 5,389,370 also adopts the methods to remove the alkylphenol compounds and proanthocyanidins described by U.S. Pat. No. 5,322,688, but it provides a method to prepare a Ginkgo biloba extract with highly concentrated active components and their combinations. The process of U.S. Pat. No. 5,389,370 is characterized in that Ginkgo biloba leaves with at least 1.4% flavone glycosides are extracted with an organic solvent selected from the group consisting of aqueous acetone, an aqueous alkanol having up to 3 C-atoms and anhydrous methanol. Most of the organic solvent is then separated from the extract to a maximum content of 10% to form a concentrated aqueous solution, which is then diluted with water to a solids content of 15–20% by weight and left to cool until a precipitate forms. This precipitate, consisting of the lipophilic components which do not dissolve well in water, is filtered off. The remaining aqueous solution is then subjected to a multi step extraction with an ester of formic acid or acetic acid, such as ethyl acetate, or a mixture of ethyl acetate with an aliphatic or cycloaliphatic hydrocarbon. The dissolved ester is removed from the remaining aqueous solution by distillation and the resultant solution is extracted with a water-immiscible C-4 or C-5 alkanol. The alkanol phases are then washed with water, then subsequently concentrated and the residual quantities of the solvent are completely removed by azeotropic distillation. The residue is then diluted with 40 weight percent ethanol and water to form a diluted residue.

In addition, to remove accompanying substances of the extract obtained with the ethyl acetate or the ethyl acetate/hydrocarbon mixture in the above process, the extract can also be treated with activated carbon or by column chromatography using silica gel.

Furthermore, the extract obtained with the ethyl acetate or the ethyl acetate/hydrocarbon mixture in the above process can first be treated with activated carbon to remove accompanying substances. Thereafter the ginkgolides are crystallized. Pure bilobalide and remaining ginkgolides are then separated from the mother liquor by column chromatography.

The diluted residue obtained at the last step in the process mentioned above can be further extracted with an aliphatic or cycloaliphatic solvent in order to reduce the alkylphenol compounds. The water phase is then concentrated and evaporated to a dry extract.

U.S. Pat. No. 5,389,370 reports that by applying the above-mentioned method, a preparation from the leaves of Ginkgo biloba can be achieved with a content of 40 to 60% flavone glycosides; 5.5–8% ginkgolides A, B, C and J and 5–7% bilobalide, or 5.5–8% ginkgolides and less than 0.1% bilobalide, or 5–7% bilobalide and a maximum of 0.1% ginkgolides; 0–10% proanthocyanidins and a maximum of 10 ppm, preferably less than 1 ppm, alkylphenol compounds.

U.S. Pat. No. 5,637,302 concerns a method for preparation of Ginkgo biloba extract in which by subjecting the crude extract of Ginkgo biloba leaves to solvent extraction with a solvent comprising toluene and n-butanol, the use of chlorinated aliphatic hydrocarbon and a lead compound are avoided. In addition, by adopting this process, the problem of other inventions of using large volumes of different solvents which are miscible with one another is also resolved. The process of U.S. Pat. No. 5,637,302 is characterized in that Ginkgo biloba leaves are extracted with an aqueous solvent comprising a mixture of acetone and water or a mixture of methanol and/or ethanol and water. These partially aqueous extracts are then extracted directly with n-hexane or n-heptane or with a toluene/butanol mixture to remove inactive lipophilic substances such as alkylphenols and polyphenols. The defatted solution is concentrated next to a volume equal to the weight of the drug and then the concentrate is kept in a refrigerator for 24 hours and then centrifuged, that produces semi-crystalline precipitate comprising a mixture of dimeric flavonoids. The aqueous phase is extracted in countercurrent with a toluene/butanol mixture in which the volume ratio of toluene:butanol varies from 1:2 to 1:4. After counterwashing with water, the toluene-butanol phase is concentrated to a paste-like consistency and taken up with water or a water-alcohol mixture in order to remove the residual traces of toluene and butanol and dried.

In addition, the aqueous solution, which has been defatted and still contains a proportion of the dimeric flavones, can be passed over absorption resins such as an aromatic polymer that readily absorbs many active substances and has a marked activity for those of a phenolic nature. The absorbed active substances are then re-eluted from the resin with an organic solvent such as a lower (C1-4) alkanol or a water-miscible ketone.

U.S. Pat. No. 5,637,302 discloses that by applying the above-mentioned methods, a preparation from the leaves of Ginkgo biloba can be achieved with a content of 22 to 26% flavone glycosides, 2.5–4.5% ginkgolides, 2.5–4.5% bilobalide, substantially free of alkylphenol compounds and less than 10% proanthocyanidins.

SUMMARY OF THE INVENTION

It is an object of the present invention to provide a more accurately defined Ginkgo biloba extract by further identifying individual components of the flavonoid compounds, determining the amount of the individual components and regulating the ratio among them. These individual components include flavonols, flavones, flavanols and flavonol glycosides. As a result, the governmental requirements for pharmaceuticals with regard to analytical definition and reproducible composition, independent from the variable composition of the starting material of Ginkgo biloba leaves, can be fulfilled. This more accurately defined Ginkgo biloba extract will also enrich its content of effective components, reduce its content of unknown elements and provide a better process and quality control standard. In addition, it will increase the safety of the pharmaceutical prepared from the extract, enhance the confidence of doctors and patients in the pharmaceutical and make screening of the drug more repeatable.

Another object of the invention is to provide a Ginkgo biloba extract with a highly concentrated effective content, that include 44 to 78% flavonoids, 2.5 to 10% ginkgolides and 2.5 to 10% bilobalide. A Ginkgo biloba extract with highly concentrated effective components is required in many countries with high pharmaceutical standards which are not usually met by simple extracts since the norms generally apply to pure substances. Until now it has not been possible to prepare such highly concentrated extracts from Ginkgo biloba leaves.

Another advantage of a Ginkgo biloba extract with highly concentrated effective content is the reduced daily dosage and smaller size of the pharmaceutical prepared from it since main applications of Ginkgo pharmaceutical are for elderly people.

An additional advantage of a Ginkgo biloba extract with highly concentrated effective content is the further removal of inactive substances. The extensive removal of inactive accompanying substances enhances the safety of the pharmaceutical, since the simpler composition of the active component concentrate facilitates a more precise analytical determination of the main components and detection of potential impurities. An extremely purified Ginkgo biloba extract is also needed in preventing organ rejection following transplants.

It is also an object of the invention to further remove ginkgolic acids in order to provide a pharmaceutical with basically no danger of allergic reactions.

Since indications for the pharmaceutical composition of Ginkgo biloba extract at present time are mainly for cerebral and peripheral arterial circulatory disturbances, it is an additional object of the invention to provide a method for applying the pharmaceutical to treat angina pectoris induced by coronary heart disease.

The invention therefore relates to a Ginkgo biloba extract with a content of 44 to 78% flavonoids, 2.5 to 10% ginkgolides A, B, C and J, 2.5 to 10% bilobalide and about 0.1 to 5 ppm ginkgolic acids.

This invention relates generally to compositions extracted from Ginkgo biloba leaves and particularly to a different composition comprising new active components and combinations, a method of preparation of the same, a method of identification and examination of individual components of the same, pharmaceuticals containing these active components and combinations, and application of the pharmaceutical to treat angina pectoris induced by coronary heart disease.

DETAILED DESCRIPTION OF THE INVENTION

This invention provides a composition comprising about 44% to about 78% flavonoids, about 2.5% to about 10% ginkgolides selected from ginkgolide A, B, C and J or a combination thereof, about 2.5% to about 10% bilobalide and about 0.1 ppm to about S ppm of ginkgolic acids.

This invention provides a composition comprising about 44% to about 78% flavonoids that include flavonols, flavanols and flavonol glycosides, about 2.5% to about 10% ginkgolides selected from ginkgolide A, B, C and J or a combination thereof, about 2.5% to about 10% bilobalide and about 0.1 ppm to about 5 ppm of ginkgolic acids.

This invention provides a composition comprising about 44% to about 78% flavonoids with a content of about 20% to about 75% flavonol glycosides, about 2.5% to about 10% ginkgolides selected from ginkgolide A, B, C and J or a combination thereof, about 2.5% to about 10% bilobalide and about 0.1 ppm to about 5 ppm of ginkgolic acids.

This invention provides a composition comprising about 44% to about 78% flavonoids which comprises flavonol glycosides and flavonols with a content ratio between flavonol glycosides and flavonols as 1–30:1, about 2.5% to about 10% ginkgolides selected from ginkgolide A, B, C and J or a combination thereof, about 2.5% to about 10% bilobalide and about 0.1 ppm to about 5 ppm of ginkgolic acids.

This invention provides a composition comprising about 44% to about 78% flavonoids comprising flavonol glycosides, about 5% to 20% of lactones, wherein the lactones comprising 2.5% to about 10% ginkgolides selected from ginkgolide A, B, C and J or mixtures thereof and about 2.5% to about 10% bilobalide wherein the ratio of flavonol glycosides to lactones is about 3.5–4.5:1 and about 0.1 ppm to 5 ppm ginkgolic acids.

This invention provides a composition comprising no less than 44% flavonoids comprising flavonol glycosides, no less than 6% lactones comprising ginkgolides selected from ginkgolides A, B, C and J or a combination thereof and bilobalide and about 0.1 ppm and 5 ppm of ginkgolic acids.

This invention provides the above compositions wherein the concentration of ginkgolic acids is about 0.1 ppm to about 0.5 ppm.

This invention provides the above compositions having components extracted from Ginkgo biloba leaves.

This invention provides the above compositions having components extracted from Ginkgo biloba leaves that are obtained from cultivated plants.

This invention provides a method for obtaining a Ginkgo biloba composition comprising steps of: (a) obtaining dried Ginkgo biloba leaves; (b) breaking the leaves into small pieces; (c) putting the broken leaves through a process of reflux in a solution selected from water, alkanols with C1 to C3, acetone and a combination thereof under conditions permitting the extraction of flavonoids and terpene lactones to produce an extract and a residue; (d) separating the extract from the residue; (e) concentrating the separated extract to a density of about 1.2 to about 1.25 at 60° C.; (f) applying the concentrate from step (e) to at least two kinds of resin under conditions permitting binding of flavonoids and lactones; (g) eluting the bound flavonoids and lactones, thereby producing an extract containing flavonoids and lactones from Ginkgo biloba.

This invention provides a method of chromatography wherein the resins are packed in columns.

This invention provides a method of chromatography wherein the resin includes, but is not limited to porous polymer, silicon gel, Aluminum oxide, polyamide, activated charcoal, cellulose and sephedax.

This invention provides a method of chromatography wherein the column is eluted with water, alkanols with C1 to C3, acetone or ester which is methyl or ethyl ester.

This invention provides a method for identification and examination of the flavones in a Ginkgo biloba composition comprising steps of: (a) preparing the assay by dissolving the composition in methanol; (b) preparing the standard by putting standard Ginkgo biloba leaves and 60% aqueous alcohol through a process of reflux; after filtration, concentrate the filtrate to evaporate off alcohol; extract the concentrated aqueous solution with petroleum, ethyl acetate and n-butanol respectively; concentrate the n-butanol portion to dryness and dissolve it in methanol; (c) performing the assay according to the TLC method by spotting each of the above-mentioned solution on the same thin silicon plate, developing the plate with a mixture of ethyl acetate, formic acid, acetic acid and water; then the plate is removed, air-dried, sprayed with 1% aluminum chloride in ethanol solution and observed under ultra-violet light at 365 nm; in both test and control chromatograms, eight yellow spots occur at the identical locations.

This invention provides a method for identification and examination of the terpene lactones in a Ginkgo biloba composition comprising steps of: (a) preparing the assay by putting the composition and ethyl acetate through a process of reflux; after filtration, concentrate the filtrate to dryness and dissolve it in methanol; (b) preparing the standard by dissolving each standard sample of ginkgolide A, ginkgolide B, ginkgolide C, ginkgolide J and bilobalide in methanol to make five standard solutions; (c) performing the assay according to the TLC method by pipetting each of the above-mentioned solutions on the same silica gel $GF_{254}$ thin layer plate respectively, developing the plate with a mixture of ethyl acetate, toluene, acetone and cyclohexane; then the plate is removed, air-dried, heated and observed under 254 nm ultra-violet light; in both test and control chromatograms spots of the same color occur at the identical locations.

This invention provides a method for identification and examination of the ginkgolic acids in a Ginkgo biloba composition comprising steps of: (a) preparing the assay by putting the composition and n-hexane through a process of reflux; after filtration, concentrate the filtrate to dryness and dissolve it in ethyl acetate; (b) preparing the standard by adding ethyl acetate to standard compounds of ginkgolic acids; (c) performing the assay according to the TLC method by pipetting each of the above mentioned solutions on the same thin-silicon-plate ($GF_{254}$); then the plate is developed with a mixture of n-hexane, ethyl-acetate and acetic acid, removed, air-dried, and observed under 315 nm and 368 nm ultra-violet; the absorbance of the sample should be less than that of the standard solution.

This invention provides a method for determination of the total amount of the flavonoids in a Ginkgo biloba composition comprising steps of: (a) preparing the standard by dissolving dry rutin with 70% aqueous alcohol; (b) obtaining the standard curve by pipetting different amount of the standard solution to a container; to each container add water, buffer (pH=4.5) of acetic acid, sodium acetate, 0.1 M aluminum chloride and 70% aqueous alcohol; plot the standard curve by obtaining the absorbance of each sample at 270 nm; (c) performing the assay according to the spectrophotometric method by dissolving the composition with 70% aqueous alcohol; pipetting the solution into a container and prepare the sample solution by using the same method described above; according to the standard curve, the concentration of the sample could be obtained by detecting its absorbance at 270 nm; the total content of flavonoids, calculated on the anhydrous basis, by rutin, is in the range of 85 to 115% of the labeled amount.

This invention provides a method for determination of the amount of the flavonol glycosides in a Ginkgo biloba composition comprising steps of: (a) preparing the assay by dissolving the composition with methanol and 25% hydrochloride and putting it through a process of reflux; then it is removed, left to cool and transferred to a container; the boiling container is washed with methanol and the washing solutions are decanted to the container, diluted to volume with methanol; (b) preparing the standard by dissolving quercetin, kaempferol and isorhamnetin in the same container; that is then diluted with methanol; (c) performing the assay by calculating the area of relative peaks on the HPLC spectrum in order to determine the amount of quercetin, kaempferol and isorhamnetin; the total amount of flavonol glycosides=amount of quercetin×2.50+amount of kaempferol×2.63+amount of isorhamnetin×2.36.

This invention provides a method for determination of the amount of the terpene lactones in a Ginkgo biloba composition comprising steps of: (a) preparing the assay by putting the composition and acetone through a process of reflux; after filtration, concentrate the filtrate and dissolve the residue in methyl acetate, followed by an extraction with water; the water layer is extracted with methyl acetate again; the two methyl acetate layers are then combined, concentrated to dryness and dissolved in methanol; (b) preparing the standard by dissolving each ginkgolide A, ginkgolide B, ginkgolide C, ginkgolide J and bilobalide with methanol in the same container; (c) performing the assay according to the HPLC test method by injecting SP and AP respectively to the column and their chromatogram are taken; the amount of ginkgolide A, ginkgolide B, ginkgolide C, ginkgolide J and bilobalide is calculated by the method for external standard in individual monograph, then they are summed up to obtain the total amount of terpene lactones.

This invention provides a method wherein the monomers of ginkgolide A, ginkgolide B, ginkgolide C, ginkgolide J and bilobalide are used as the standards to identify the terpene lactones in a Ginkgo biloba composition.

This invention provides a method wherein the monomers of Ginkgolic acids are used as the standards to identify the Ginkgolic acids in a Ginkgo biloba composition.

This invention provides a method wherein the monomer of rutin is used as the standard to determine the total amount of flavonoids in a Ginkgo biloba composition.

This invention provides a method wherein the monomers of quercetin, kaempferol, isorhamnetin are used as the standards to determine the amount of flavonols and flavonol glycosides in a Ginkgo biloba composition.

This invention provides a method wherein the monomers of ginkgolide A, ginkgolide B, ginkgolide C, ginkgolide J and bilobalide are used as the standards to determine the amount of the terpene lactones in a Ginkgo biloba composition.

This invention provides the above compositions that can be used as food additive or added into beverages.

This invention provides the above compositions that can be added into cream, ointments or presence in the raw materials to prepare the same.

This invention provides an oral formulation containing the above compositions.

This invention provides the above oral formulation that can take the form of pill, capsule, granule, tablet or a suspension.

This invention provides an injectable formulation containing the above compositions. The injectable formulation may then be administered to a subject via different routes, such as intravenous injection, intramuscular injection, dermal injection and peritoneal injection.

This invention provides a cosmetic formulation containing the above compositions.

This invention provides a pharmaceutical composition prepared according to the above methods, which comprises an effective amount of the above compositions and a pharmaceutically acceptable carrier.

For the purposes of this invention, "pharmaceutically acceptable carriers" means any of the standard pharmaceutical carriers. Examples of suitable carriers are well known in the art and may include, but not limited to, any of the standard pharmaceutical carriers such as a phosphate buffered saline solutions, phosphate buffered saline containing Polysorb 80, water, emulsions such as oil/water emulsion and various type of wetting agents. Other carriers may also include sterile solutions, tablets, coated tablets pharmaceutical and capsules.

Typically such carriers contain excipient such as starch, milk, sugar, certain types of clay, gelatin, stearic acid or salts thereof, magnesium or calcium stearate, talc, vegetable fats or oils, gums, glycols or other known excipient. Such carriers may also include flavor and color additives or other ingredients. Compositions comprising such carriers are formulated by well known conventional methods.

This invention provides a method for treating angina pectoris of various kinds and degrees induced by coronary heart disease by administering to a subject an effective amount of the above pharmaceutical compositions.

This invention provides a method for improving ischemic electrocardiogram by administering to a subject an effective amount of the above pharmaceutical compositions.

This invention provides a method for relieving angina pectoris by administering to a subject an effective amount of the above pharmaceutical compositions.

This invention provides a method for reducing the usage of nitroglycerin by administering to a subject an effective amount of the above pharmaceutical compositions.

This invention provides a method for relieving palpitation by administering to a subject an effective amount of the above pharmaceutical compositions.

This invention provides a method for decreasing cholesterol and triglyceride level in blood for a subject with abnormal blood-lipid by administering to the subject an effective amount of the above pharmaceutical compositions.

This invention provides a method for decreasing platelet aggregation in blood by administering to a subject an effective amount of the above pharmaceutical compositions.

This invention provides a method for improving exercise tolerance and extending exercise duration, interval between exercise initiation and angina occurrence and interval between exercise initiation and 1 mm. decrease of ST segment by administering to a subject an effective amount of the above pharmaceutical compositions.

This invention provides a method for treating impotence by administering to a subject an effective amount of the above pharmaceutical compositions.

This invention provides a method for treating psoriasis by administering to a subject an effective amount of the above pharmaceutical compositions.

This invention provides a method for treating pigment precipitation by administering to a subject an effective amount of the above pharmaceutical compositions.

This invention also provides a method for treating absent-mindedness, AIDS, Alzheimer's disease, angina pectoris, arteriosclerosis, arthritis, asthma, atherosclerosis, autism, bed-wetting, brain trauma, cardiac disorders, chilblain, chills, coronary heart disease, deafness, dementia, depression, diabetic vasoconstriction with gangrene and angina, dizziness, eye disorders, failing memory, fatigue, filariasis, headache, hypercholesterolemia, hypertension, intermittent claudication, kidney disorders, leg cramps, myocardial infarction, Parkinson's disease, poor circulation, postthrombotic syndrome, Raynaud's syndrome, rheumatism, senility, thorax suffocation, tinnitus aurium, tuberculosis, varicose veins and vertigo by administering to a subject an effective amount of the above pharmaceutical compositions.

The above pharmaceutical compositions can be used for these therapeutic purposes because they have the actions of anodyne, antasthmatic, anti-inflammatory, antiatherogenic, antibacterial, anti-cancer, anticoagulant, antidiabetic, antihypercholesterolemic, antihypertensive, anti-nuclear radiation, anti-platelet aggregation, antioxidant, antithrombotic, antituberculotic, antitussive, bronchodilator, capillary protectant, cerebral circulatory stimulant, cerebral vasodilator, improving concentration, improving memory, improving hearing, improving peripheral circulation, increasing level of dopamine, epinephrine and norepinephrine, neurotransmitter modulator, preventing atherosclerosis of the carotid arteries and vasodilator.

This invention will be better understood from the examples which follow. However, one skilled in the art will readily appreciate that the specific methods and results discussed are merely illustrative of the invention as described more fully in the claims which follow thereafter.

Experimental Details

EXAMPLE 1

This invention provides a method for preparation of a Ginkgo biloba composition comprising steps of: (a) extraction: green Ginkgo biloba leaves harvested from late summer to early autumn with the highest concentration of active therapeutic components and less than 8% of water are dried and crushed in a mill to a particle size of less than 4 mm; the leaves are then subjected to a process of reflux twice under normal pressure, each for 3 hours in 12 times the volume of 60% aqueous alcohol; the solid residue is separated by filtration and undergoes the third reflux for 0.5 hours in 10 times the volume of water; the above-mentioned three filtrates are then combined; (b) concentration: the filtrate from step (a) is concentrated under vacuum pressure to thick extract without alcohol (d=1.2–1.25, t=60° C.); (c) precipitation: the thick extract from step (b) is dissolved in 2 times the volume of boiling water and allowed to cool to form a precipitate and then it is separated by filtration; (d) chromatography: the filtrate from step (c) is subjected to a porous polymer (XAD-4) column, with a rate of resin to leaves as 1:1; then it is eluted with pure water and 6%, 18%, and 30% aqueous alcohol respectively in double volume of the filtrate; finally the column is eluted with 65% aqueous alcohol until the color of the eluate becomes light; the 18% eluate and 30% eluate are combined and concentrated under vacuum pressure to small volume without alcohol; the concentrate is then put through a polyamide column and the amount of the polyamide is one third of that of the crude leaves; the concentrate is next eluted with pure water and 95% aqueous alcohol respectively, and the 95% eluate is combined with the 65% eluate from the porous polymer column; the combination is concentrated under vacuum pressure (e) elimination of ginkgolic acids: the concentrate from step (d) is extracted with two thirds the volume of cyclohexane three times; the water portions are concentrated under vacuum pressure; (f) dry: the density of the concentrated extract is adjusted to 1.05 and then dry-sprayed; the temperature of the spray-tank is controlled at 140–160° C.

The product is yellow or brown powder, especially fragrant and a little bit bitter.

In an embodiment of the preceding method, the process of chromatography is characterized by a double treatment operation which subjects the extract first to a porous polymer (XAD-4) column with a rate of resin to leaves as 1:1, then to a polyamide column with a rate of polyamide to leave as 1:3.

In a separate embodiment of the method, the process of removing the ginkgolic acids is characterized by a double treatment operation which subjects the extract first to a porous polymer (XAD-4) column, then to cyclohexane for three times.

EXAMPLE 2

This invention provides a method for preparation of a Ginkgo biloba composition comprising steps of: (a) extraction: green Ginkgo biloba leaves harvested from late summer to early autumn with the highest concentration of active therapeutic components and less than 8% of water are dried and crushed in a mill to a particle size of less than 4 mm; the leaves are then subjected to a process of reflux three times under reduced pressure, each for 1–3 hours in 12 times the volume of one solvent system selected from water, water- EtOH and acetone-water; the solid residue is separated by filtration; the above mentioned three filtrates are then combined; (b) concentration: the filtrates from step (a) is concentrated under vacuum pressure to thick extract without organic solvent (d=1.2–1.25, t=60° C.); (c) precipitation: the thick extract from step (b) is dissolved in 2 times the volume of boiling water and allowed to cool to about 12° C. to form a precipitate and then it is separated by filtration; (d) chromatography: the filtrate from step (c) is subjected to one kind of resin column; then it is eluted with pure water or mixture of water and organic solvents selected from alcohol with C1–C3 and acetone; the portions of eluate are concentrated and then subjected to another kind of resin column; then the column is eluted with one or two solvent system selected from water, alcohol with C1–C3, ketone and ester; the portions of eluate containing high content of lactones and flavonoids are obtained and then concentrated under reduced pressure to get rid of aqueous alcohol; (e) elimination of ginkgolic acids: the concentrate from step (d) is extracted with ⅔ the volume of saturated or unsaturated alkane three times; the water portions are concentrated under vacuum pressure; (f) dry: the density of the concentrated extract is adjusted to 1.02–1.10 (40° C.) and then dry-sprayed; the temperature of the spray-tank is controlled at 140–160° C.

EXAMPLE 3

This invention provides a method for preparation of a Ginkgo biloba composition comprising steps of: Put 100 kg. of dry Ginkgo biloba leave powder and 1,000 kg. of 50% aqueous alcohol through a progress of reflux for two hours. Filter the extract. Put the residue and 1,000 kg. of 50% aqueous alcohol through a process of reflux for the second time for two hours and filter the extract. The two portions of filtrate are then combined and concentrated under vacuum pressure at 60° C. to thick extract without alcohol (d=1.2). The thick extract is then dissolved in 300 kg. of water and left to stand for 48 hours. Filter the extract again. The filtrate is subjected to a column with a mixed resin of porous polymer and polyamide, eluted with 100 kg. of water, 100 kg. of 30% aqueous alcohol, 100 kg. of 60% and 90% aqueous alcohol respectively. Combine 30% portion, 60% portion and 90% portion aqueous alcohol eluate. The combination is concentrated under vacuum pressure to about 70 kg. of thick extract. The thick extract is partitioned with n-hexane three times. The water phases are concentrated and dried under vacuum pressure. 1.5 kg. of final product with less than 5% of water is obtained, which contains 47.2% content of flavonoids wherein flavonol glycosides is 24.8%, lactones is 6.3% and less than 5 ppm of ginkgolic acids.

EXAMPLE 4

Start with column chromatography in example 3. The 30% aqueous alcohol eluate from the column is concentrated under reduced pressure to get rid of alcohol. The concentrate is extracted three times, each time with ⅔ of its volume of ethyl acetate. The ethyl acetate phases are concentrated under reduced pressure and evaporated at about 45° C. The residue is dissolved in 50% aqueous alcohol at boiling temperature then allowed to stand for 24 hours, ginkgolides crystal forms. After separation of the crystals, the mother liquor is evaporated under reduced pressure and separated by column chromatography with 1.5 times its weight of activated carbon and silica gel respectively. All of the fractions containing bilobalide and ginkgolides are collected separately, concentrated to dryness and combined with the ginkgolides crystal 10 g. (A). The total amount of terpene lactone is no less than 80% by weight (A).

Collect and combine the 60% portion and 90% portion of aqueous alcohol eluate from the column in Example 3. Concentrate under reduced pressure to remove the alcohol completely. The concentrate are applied to a polyamide column, which is eluted with 10%, 20%, 75% and 90% aqueous alcohol respectively. The 75% eluate is concentrated to dryness. The powder is dissolved in anhydrous alcohol and subjected to polyamide column eluted with 100% alcohol, 70% aqueous alcohol and 20% aqueous alcohol separately. The 70% eluate is collected and mixed with 2 kg. of silica gel. The mixture is concentrated to dryness and eluted with EtOAc, alcohol respectively. The alcohol portion is concentrated to dryness (B) 90 g. The total amount of flavonoids is no less than 80% by weight.

The high content extracts of lactones (A) and flavonoids (B) are mixed in different ratio to obtain different content final products, such as 10 g. (A) +90 g. (B) =100 g. (A+B) which contains 77% flavonoids and 8% terpene lactones. 10 g. (A) +70 g. (B) =80 g. (A+B) This product contains 70% flavonoids and 10% lactones.

EXAMPLE 5

Methods for identification and examination of the flavones, the terpene lactones and the ginkgolic acids and methods for determining the total amount of the flavonoids, the flavonol glycosides and the terpene lactones.

This invention provides a method for identification and examination of the flavones in a Ginkgo biloba composition comprising steps of: (a) preparing the assay by dissolving 0.1 g. of the composition in 1 ml. of methanol; (b) preparing the standard by putting 1 g. of standard Ginkgo biloba leaves an d 10 ml. of 60% aqueous alcohol through a process of reflux for 2 hours; after filtration, concentrate the filtrate to evaporate off alcohol; extract the concentrated aqueous solution with 10 ml. petroleum, 10 ml. ethyl acetate and 10 ml. n-butanol respectively; concentrate the n-butanol portion to dryness and dissolve it in 1 ml. of methanol; (c) carrying out the assay by spotting 10 µl. each of the above-mentioned solution on the same thin silicon plate, developing the plate with a mixture of ethyl acetate, formic acid, acetic acid and water (100:11:11:26); then the plate is removed, air-dried, sprayed with 1% aluminum chloride in ethanol solution and observed under ultra-violet light at 365 nm; in both test and control chromatogram, eight yellow spots occur at the identical locations.

This invention provides a method for identification and examination of the terpene lactones in a Ginkgo biloba composition comprising steps of: (a) preparing the assay by putting 0.5 g. of the composition and 20 ml. of ethyl acetate through a process of reflux for 30 minutes; after filtration, concentrate the filtrate to dryness and dissolve it in 2 ml. methanol; (b) preparing the standard by dissolving each standard sample of ginkgolide A, ginkgolide B, ginkgolide C, ginkgolide J, and bilobalide in methanol to make five standard solutions of 1 ml. containing 0.5 mg. each; (c) carrying out the assay by pipetting 10 µl. of each of the above-mentioned solutions on the same silica gel $GF_{254}$ thin layer plate respectively, developing the plate with a mixture of ethyl acetate, toluene, acetone and cyclohexane (4:3:2:1); then the plate is removed, air-dried, heated at 150° C. for an hour and observed under 254 nm ultra-violet light; in both test and control chromatogram spots of the same color occur at the identical locations.

This invention provides a method for identification and examination of the ginkgolic acids in a Ginkgo biloba composition comprising steps of: (a) preparing the assay by putting 4 g. of the composition and 100 ml. of n-hexane through a process of reflux for 2 hours; after filtration, concentrate the filtrate to dryness and dissolve it in 1 ml. of ethyl acetate; (b) preparing the standard by adding ethyl acetate to standard compounds of ginkgolic acids to make a solution of 0.04 mg. in 1 ml; (c) carrying out the assay by pipetting 10 μl. of each of the above mentioned solutions on the same thin-silicon-plate (GF254) respectively; then the plate is developed with a mixture of n-hexane, ethyl-acetate and acetic acid (80:15:5), removed, air-dried and observed under 315 nm and 368 nm ultra-violet respectively; the absorbance of the sample should be less than that of the standard solution (0.0005%).

This invention provides a method for determination of the total amount of flavonoids in a Ginkgo biloba composition comprising steps of: (a) preparing the standard by dissolving 20 mg. of dry rutin with 70 ml. of 70% aqueous alcohol; (b) obtaining the standard curve by pipetting 0.2, 0.4, 0.6, 0.8, 1.0, 1.2 ml. of this standard solution each to a 10 ml. volumetric flask; to each flask add 3 ml. of water, 2 ml. of buffer (pH=4.5) of acetic acid, sodium acetate, 2 ml. of 0.1 M aluminum chloride and 70% aqueous alcohol to make 10 ml. total volume for each flask; plot the standard curve by obtaining the absorbance of each sample at 270 nm; (c) carrying out the assay according to the spectrophotometric method by dissolving 25 mg. of the composition with 70% aqueous alcohol in a 50 ml. volumetric flask; pipetting 0.5 ml. of this solution into a 10 ml. volumetric flask and prepare the sample solution by using the same method described above; according to the standard curve, the concentration of the sample could be obtained by detecting its absorbance at 270 nm; the content of total flavonoids, calculated on the anhydrous basis, by rutin, is in the range of 85%–115% of the labeled amount.

This invention provides a method for determination of the amount of the flavonol glycosides in a Ginkgo biloba composition comprising steps of: (a) preparing the assay by dissolving 75 mg. of the composition with 20 ml. of methanol and 5 ml. of 25% hydrochloride and putting it through a process of reflux for 60 minutes; then it is removed, left to cool and immediately transferred to a 50 ml. volumetric flask; the boiling flask is washed with three 5 ml. portions of methanol and the washing solutions are decanted to the volumetric flask, diluted to volume with methanol; (b) preparing the standard by dissolving 4.2 mg. of quercetin, 6.0 mg. of kaempferol and 1.2 mg. of isorhamnetin in the same 50 ml. volumetric flask, that is then diluted with methanol; the standard 1 ml. containing 84 μg. of quercetin, 120 μg. of kaempferol and 24 μg. of isorhamnetin is obtained; (c) carrying out the assay by calculating the area of relative peaks on the HPLC spectrum in order to determine the amount of quercetin; kaempferol and isorhamnetin; the total amount of flavonol glycosides=amount of quercetin×2.50+amount of kaempferol×2.63+amount of isorhamnetin×2.36.

This invention provides a method for determination of the amount of the terpene lactones in a Ginkgo biloba composition comprising steps of: (a) preparing the assay by putting 100 mg. of the composition and 60 ml. of acetone through a process of reflux for 2 hours; after filtration, concentrate the filtrate and dissolve the residue in 20 ml. of methyl acetate, followed by an extraction with 10 ml. of water; the water layer is extracted with 20 ml. of methyl acetate again; the two methyl acetate layers are combined, concentrated to dryness and dissolved in 5 ml. of methanol; (b) preparing the standard by dissolving 30 mg. of each ginkgolide A, ginkgolide B, ginkgolide C, ginkgolide J and bilobalide with methanol in the same 50 ml. volumetric flask; (c) carrying out the assay by injecting 15 μl. SP and AP respectively to the column and their chromatograms are taken; the amount of ginkgolide A, ginkgolide B, ginkgolide C, ginkgolide J and bilobalide is calculated by the method for external standard in individual monograph, then they are summed up to obtain the total amount of terpene lactones; calculation is carried out on an anhydrous basis and the total amount of the terpene lactones in the extract is about 5–20%.

In an embodiment of the above methods, the monomer of rutin, which is highly purified and with a clear chemical structure ($C_{27}H_{30}O_{16}$), is used as the standard to determine the total amount of the flavonoids in a Ginkgo biloba composition.

In an embodiment of the above methods, the monomers of quercetin, kaempferol, isorhamnetin, that are highly purified and with clear chemical structures, are used as the standards to determine the amount: of flavonols and flavonol glycosides in a Ginkgo biloba composition.

In an embodiment of the above: methods, the monomer of catechin, which is highly purified and with a clear chemical structure, is used as the standard to determine the amount of the flavanols in a Ginkgo biloba composition.

In an embodiment of the above methods, the monomers of ginkgolide A, ginkgolide B, ginkgolide C, ginkgolide J and bilobalide, that are highly purified and with clear chemical structures, are used as the standards to identify the terpene lactones and determine the amount of the terpene lactones in a Ginkgo biloba composition.

In an embodiment of the above methods, the monomers of Ginkgolic acids, that are highly purified and with clear chemical structure, are used as the standards to identify the ginkgolic acids in a Ginkgo biloba composition.

EXAMPLE 6

Coated tablets

| 1 table contains: | | |
|---|---|---|
| Ginkgo Biloba extract | * | 40.00 mg. |
| Lactose | * | 100.00 mg. |
| Starch | * | 40.00 mg. |
| Microcrystalline cellulose | * | 36.00 mg. |
| Hydroxypropyl methylcellulose | * | 30.00 mg. |
| Magnesium stearate | * | 1.50 mg. |
| OPADRY (in coat) | * | 7.50 mg. |
| Weight of a coated tablet | Approx. | 255.00 mg. |

EXAMPLE 7

| Granules 1 sachet contains: | | |
|---|---|---|
| Ginkgo biloba extract | * | 40.00 mg. |
| Sucrose | * | 420.00 mg. |
| Dextrine | * | 480.00 mg. |
| Starch | * | 20.00 mg. |
| Hydroxypropyl cellulose | * | 20.00 mg. |
| Sterioside | * | 20.00 mg. |
| Weight of a sachet | Approx. | 1000.00 mg. |

EXAMPLE 8

| Injection 1 ampule contains: | | |
|---|---|---|
| Ginkgo biloba extract | * | 40.00 mg. |
| Mannitol | * | 100.00 mg. |
| Nicotinamide | * | 100.00 mg. |
| Arginine monohydrochloride | * | 50.00 mg. |
| EDTA-2Na | * | 4.00 mg. |

EXAMPLE 9

| Drink 500 ml. drink contains: | | |
|---|---|---|
| Ginkgo biloba extract | * | 2.0 g. |
| 38% alcohol | * | 500.0 ml. |
| Spicery | * | proper amount |

Experimental Data

The Ginkgo biloba extract described in this invention can be processed in the usual way for preparation of pharmaceuticals, e.g. to solutions, coated tablets, tablets or injection preparations. The pharmaceuticals of the invention can be used for treating cerebral and peripheral arterial circulatory disturbances. In particular, the Ginkgo pharmaceutical composition can be applied for therapeutic purposes on angina pectoris induced by coronary artery disease. Clinical trials conducted in China for this invention on 243 patients have proved that the Ginkgo biloba extract described above is safe and effective for human use in treating angina pectoris induced by coronary artery disease. Details of the clinical trials can be summarized as follows:

Participating Hospitals

Four hospitals took part in the clinical trials. The participating hospitals were the Dongzhimen Hospital affiliated with the Beijing Traditional Chinese Medicine College, the Huashan Hospital affiliated with the Medical University of Shanghai, the Ninth People's Hospital affiliated with the Second Medical University of Shanghai and the Longhua Hospital affiliated with the Shanghai Traditional Chinese Medicine College.

Selection Criteria for Patients

The clinical trials were conducted from November, 1995 to July, 1996, in which 243 patients with a diagnosis of angina pectoris induced by coronary artery disease participated according to pre-determined inclusion and exclusion criteria, that were as follows:

Inclusion Criteria:

Patients with clear angina pectoris diagnosis. The chest pain attacked more than two times a week. Ischemia changed on electrocardiogram or results of stress testing were positive.

Exclusion Criteria:

(1) patients with active myocardial infarct or other cardiopulmonary heart disease, such as severe psychoneurosis, menopuasal syndrome and chest pain caused by cervical spondylopathy; (2) patients of angina pectoris combined with hypertension (BP>24/14.87 Kpa); (3) patients of severe cardiopulmonary function deficiency, severe arrhythmia, abnormal of liver and renal function and disease of hematopoietic; (4) breast-feeding women and patients of allergic diathesis; (5) patients younger than 18 or older than 70.

Criteria of Dropping-out:

Patients were dropped from the study if they did not take the medicine as prescribed or if the data were incomplete because the patients did not follow the instructions in the trial protocol. The total effective rate of relieving angina pectoris was 92.2% within the range 90–93.6% and that of improving ischemic electrocardiogram was 62.6%.

Of the 243 patients enrolled, researchers randomized 153 patients into a Ginkgo group and 90 patients into a control group. They then split the Ginkgo group, randomizing 123 patients into a test group and 30 into an open group. Double-blind method was adopted for 213 cases in the test and control group, but for the open group with 30 cases. Examples of base-line characteristics of the 243 patients enrolled in 4 hospitals are presented below (Tab. 1—Tab. 5). The chi-square results showed that there was no significant difference among these three groups in age, sex, duration of illness, type and seriousness of angina pectoris and complication. The rate of hospital admission was 72.4%.

TABLE 1

Distribution of Sex and Mean Value of Age in 3 Groups, $P > 0.05$

| Group | Number | Sex M | Sex F | Sex (%) M | Sex (%) F | Age (X ± SD) |
|---|---|---|---|---|---|---|
| Test | 123 | 76 | 47 | 62 | 38 | 62.1 ± 5.8 |
| Control | 90 | 61 | 29 | 68 | 32 | 62.8 ± 5.8 |
| Open | 30 | 17 | 13 | 57 | 43 | 62.7 ± 7.2 |

TABLE 2

Duration of Illness of Patients in 3 Groups, $P > 0.05$

| Group | Case | 1 m. ~ | 6 m. ~ | 1 yr. ~ | 3 yr. ~ | 5 yr. ~ | 10 yr. ~ |
|---|---|---|---|---|---|---|---|
| Test | 123 | 6 | 8 | 26 | 28 | 24 | 32 |
| Control | 90 | 6 | 8 | 14 | 15 | 33 | 14 |
| Open | 30 | 3 | 1 | 3 | 8 | 8 | 7 |

TABLE 3

Seriousness of Angina Pectoris in 3 Groups, $P > 0.05$

| Group | Case | Low-grade | Mid-grade | High-grade |
|---|---|---|---|---|
| Test | 123 | 24 | 84 | 15 |
| Control | 90 | 24 | 53 | 13 |
| Open | 30 | 6 | 16 | 8 |

TABLE 4

Types of Angina Pectoris in 3 Groups, $P > 0.05$

| Group | Case | Tiredness-induced | Spontaneous | Mixture |
|---|---|---|---|---|
| Test | 123 | 96 | 8 | 19 |
| Control | 90 | 67 | 5 | 18 |
| Open | 30 | 23 | 3 | 4 |

TABLE 5

Complication of Angina Pectoris in 3 Groups, P > 0.05

| Group | Case | Hypertension | Diabetes | Hyperlipemia |
|---|---|---|---|---|
| Test | 123 | 34 | 4 | 26 |
| Control | 90 | 25 | 3 | 23 |
| Open | 30 | 9 | 0 | 14 |

Diagnostic Standard
1. Diagnostic Standard for Angina Pectoris Severity

The diagnostic standard for angina pectoris severity used in the clinical trials was based on the Criteria for Assessment of Clinical Electrocardiographic Efficacy in Patients with Angina Pectoris due to Coronary Artery Disease reported at the symposium on treating angina pectoris and arrhythmia due to coronary artery disease by integration of western and Chinese traditional medicines in 1979. The standard is as follows:

1. Low-grade: Typical attack of angina pectoris, which usually lasts a few minutes and occurs 1–3 times a day or 2–3 times a week. The attack is not severe, but the patient sometimes needs to take nitroglycerin.

2. Mid-grade: Angina attack occurs more than 3 times everyday, which lasts several to ten minutes every time. The pain is more severe than that of the low-grade attack and the patient generally needs sublingual nitroglycerin.

3. High-grade: Angina attack occurs frequently daily. It lasts longer and more seriously. Routine life is affected. The patient needs to use nitroglycerin frequently.

2. Diagnostic Standard for Angina Pectoris Types

The diagnostic standard for angina pectoris types used in the clinical trials was in accordance with the Diagnostic Criteria and Determination of Ischemic Heart Disease issued by the Co-committee of the International Society of Cardiology and the Standardization of Clinical Determination of the World Health Organization. The standard is as follows:

1. Tiredness-induced Angina pectoris: The transient attack of chest pain is caused typically by exertion or other conditions that increase myocardial oxygen demands. The pain normally disappear rapidly after rest or administration of sublingual nitroglycerin.

2. Spontaneous angina pectoris: The attack of chest pain is not obviously related to increase of myocardial oxygen consumption. Compared with tiredness-induced angina pectoris, the pain lasts longer and is more severe. It can not be easily alleviated by nitroglycerin.

3. Mixed Angina Pectoris: Spontaneous angina pectoris can come with tiredness-induced angina pectoris, which is classified as mixed angina pectoris.

Design of Clinical Trials

The clinical trials were conducted as follows: 243 patients with angina pectoris induced by coronary artery disease participated in the clinical trials. Researchers randomized 153 patients into a Ginkgo group and 90 patients into a control group. They then split the Ginkgo group, randomizing 123 patients into a test group and 30 into an open group. Double-blind method was adopted for 213 cases in the test and control group, but not for the open group with 30 cases. Medicine -used at the Ginkgo group was the pharmaceutical composition of Ginkgo biloba extract described in this invention. 1 g. of the pharmaceutical composition consists of 40 mg. of Ginkgo biloba extract, 480 mg. of dextrin, 420 mg. of sucrose, 20 mg. of starch, 20 mg. of low substitute hydroxypropyl cellulose and 20 mg. of stevioside. The Ginkgo pharmaceutical composition takes the form of granule and is packed in small sachets, each of which contains 1 g. of the composition. At the clinical trial, patients took 1 sachet of the Ginkgo pharmaceutical composition each time and 3 times a day. The course of the therapy was six weeks.

The medicine used for the control group was Brainway® produced by Shanghai Sine Laboratories, which is located at No. 71, North Sichuan Road, Shanghai, the People's Republic of China. Brainway® takes the formulation of capsule. At the clinical trial, patients took 1 capsule of Brainway® each time and 3 times a day as a positive control. The course of the therapy was also six weeks.

Since formulations of the two medicines used at the clinical trials were different (granules of Ginkgo pharmaceutical composition vs. capsules of Brainway®), the double dummy with the same appearance was used for both groups. Placebo in the appearance of a capsule was used by the Ginkgo group in addition to the Ginkgo pharmaceutical composition. Placebo in the appearance of sachet was used by the control group in addition to Brainway®. The appearance and dosage of the placebos were exactly the same as those of the corresponding medicine.

For one week before the clinical trials long-effect coronary heart disease medicine was prohibited. Patients with mild hypertension were allowed to take the medicine they used before. Nitroglycerin could be temporarily used if patients could not bear angina pectoris attacks.

The Standard for Assessment of Drug Efficacy

The assessment standard for the effect of the medicines was in accordance with the Guidelines for Clinical Trials on New Chinese Traditional Medications Treating Patients with Angina Pectoris due to Coronary Artery Disease issued by the Ministry of Health of China in 1993, and the Criteria for Assessment of Clinical Electrocardiographic Efficacy in Patients with Angina Pectoris due to Coronary Artery Disease reported at the symposium on treating angina pectoris and arrhythmia due to coronary artery disease by integration of western and Chinese traditional medicines in 1979. The standard is as follows:

For patients with low-grade angina pectoris: (1) Markedly effective: Angina disappeared or basically disappeared; (2) Effective: Angina attack was obviously alleviated; (3) No effect: Angina symptoms did not improve; (4) Deterioration: Angina symptoms was aggravated, reaching the level of mid-grade angina pectoris.

For patients with mid-grade angina pectoris: (1) Markedly effective: Angina disappeared; (2) Effective: Angina symptoms were alleviated and met the criteria for low-grade angina pectoris; (3) No effect: Angina symptoms did not improve; (4) Deterioration: intensified, reaching the high-grade level.

For patients with high-grade angina pectoris: (1) Markedly effective: Angina symptoms disappeared or was alleviated and met the criteria for low-grade angina pectoris; (2) Effective: Angina symptoms were obviously alleviated and met the criteria for mid-grade angina pectoris; (3) No effect: Angina symptoms did not improve; (4)Deterioration: Angina symptoms intensified and met the criteria for severe angina pectoris.

The standard for measuring the effect of the two medicines on patients by electrocardiogram: (1) Markedly effective: Electrocardiogram returned to normal or approximately normal level; (2) Effective: ST segment went down and returned to 0.05 mv and above, but did not reach the normal level. The inverted T wave of main lead became shallow more than 25% or changed from flatness to uprightness. There was improvement on atrioventricular block or intraventricular block; (3) No effect: No improvement on electrocardiogram was observed; (4)Deterioration: ST segment decreased greatly and T wave became inverted. There occurred ectopic cardiac rhythm or arrhythmia.

The formula for calculating the ratio of stopping nitroglycerin usage is: the number of patients who stop nitroglycerin usage after the therapy/the number patients who use nitroglycerin before the therapy×100%.

Conclusions of the Clinical Trials

At the clinical trial, no obvious side effects were observed in the Ginkgo group and the control group. only three patients had gastric discomfort during the therapy. Among them, one had slight nausea and relaxed without management.

From the data obtained in the randomized, controlled, double blind or open clinical trials, it is concluded that the pharmaceutical composition of Ginkgo biloba extract described in this invention is safe and effective in treating angina pectoris due to coronary artery disease. The pharmaceutical composition of Ginkgo biloba extract has showed substantial bioactivity that is superior in one or more aspects in terms of safety and efficacy when compared with existing herbal medicines in treating angina pectoris. It can also reduce the usage of nitroglycerin.

1. The pharmaceutical composition of Ginkgo biloba extract described in this invention is effective in treating angina pectoris induced by coronary artery disease and its markedly effective rate is significantly higher than that of the control drug.

TABLE 6

Effects of the Pharmaceutical Composition of Ginkgo Biloba Extract on Angina Pectoris after Medication

| Group | Number | Markedly Effective | Effective | No Effect | Deterioration | Total Effective Rate |
| --- | --- | --- | --- | --- | --- | --- |
| Test | 123 | 47(38.2) | 66(53.7) | 10(8.1) | 0 | 91.9%** |
| Control | 90 | 14(15.6) | 56(62.2) | 20(22.2) | 0 | 77.8% |
| Open | 30 | 13(43.3) | 15(50) | 2(6.7) | 0 | 93.3%* |

**$P < 0.01$ as compared with the control; *$P < 0.05$

2. The pharmaceutical composition of Ginkgo biloba extract described in this invention is effective in improving ischemic electrocardiogram and its effective rate is higher than that of the control drug.

TABLE 7

Effects of the Pharmaceutical Composition of Ginkgo Biloba Extract on Improving Ischemic Electrocardiogram

| Group | Number | Markedly Effective | Effective | No Effect | Deterioration | Total Effective Rate |
| --- | --- | --- | --- | --- | --- | --- |
| Test | 117 | 22(18.8) | 50(42.7) | 44(37.6) | 1 | 61.5% |
| Control | 86 | 7(8.1) | 39(45.3) | 39(45.3) | 1 | 53.5% |
| Open | 30 | 6(20) | 14(46.6) | 10(33.3) | 0 | 66.7% |

3. The pharmaceutical composition of Ginkgo biloba extract described in this invention is effective in relieving angina pectoris and it is better than the control drug in reducing nitroglycerin usage.

TABLE 8

Effects of the Pharmaceutical Composition of Ginkgo Biloba Extract on Reducing nitroglycerin Usage

| Group | Number | No. Of Pre-medication User | No. Of Post-medication Withdraw | No. Of Reduction | Reduction Rate |
| --- | --- | --- | --- | --- | --- |
| Test | 123 | 111 | 63(56.8) | 33(29.7) | 86.5%* |
| Control | 90 | 82 | 28(34.1) | 16(19.5) | 53.7% |
| Open | 30 | 27 | 18(66.7) | 7(25.9) | 92.5%* |

*$P < 0.01$ as compared with the control

4. The pharmaceutical composition of Ginkgo biloba extract described in this invention is effective in relieving palpitation and its effective rate is higher than that of the control drug.

TABLE 9

Effects of the Pharmaceutical Composition of Ginkgo Biloba Extract on Improving Angina Pectoris Symptoms after Medication

| Group | Item | Palpitation | Chest Distress |
| --- | --- | --- | --- |
| Test | Pre-medication | 110 | 107 |
|  | Effective (%) | 70(63.6) | 65(63.1) |
|  | Disappearance (%) | 26(20.9)* | 24(33) |
| Control | Pre-medication | 23 | 67 |
|  | Effective (%) | 34(44.7) | 31(46.3) |
|  | Disappearance (%) | 11(14.5) | 22(32.8) |
| Open | Pre-medication | 20 | 29 |
|  | Effective (%) | 6(30) | 13(44.8) |
|  | Disappearance (%) | 13(65)* | 15(51.2) |

*$P < 0.01$ as compared with the control

5. The pharmaceutical composition of Ginkgo biloba extract described in this invention is effective in reducing cholesterol and triglyceride level in blood for patients with abnormal blood-lipid.

TABLE 10

Effects of the Pharmaceutical Composition of Ginkgo Biloba Extract on Blood-lipid Change in Patients with Abnormal Blood-lipid

| Item | No. | Pre-medication | Post-medication |
| --- | --- | --- | --- |
| Cholesterol | 56 | 6.57 ± 0.93 | 6.01 ± 1.25* |
| Triglyceride | 94 | 2.46 ± 0.85 | 2.31 ± 0.79* |
| Low Density Lipoprotein | 75 | 4.15 ± 0.64 | 3.81 ± 1.11 |

*$P < 0.05$ as compared with pre-medication

6. The pharmaceutical composition of Ginkgo biloba extract described in this invention is effective in decreasing platelet aggregation in blood and the difference is significant between pre- and post medication.

TABLE 11

Effects of the Pharmaceutical Composition of Ginkgo Biloba Extract on Patients' Hemorheological Change

| Item | Test | | | Control | | |
| --- | --- | --- | --- | --- | --- | --- |
|  | No | Pre-med | Post-med | No | Pre-med | Post-med |
| Serum Viscosity | 93 | 1.74 ± 0.30 | 1.73 ± 0.17 | 30 | 1.81 ± 0.17 | 1.74 ± 0.16 |

TABLE 11-continued

Effects of the Pharmaceutical Composition of
Ginkgo Biloba Extract on Patients' Hemorheological Change

|  | Test | | | Control | | |
|---|---|---|---|---|---|---|
| Item | No | Pre-med | Post-med | No | Pre-med | Post-med |
| Platelet Aggregation Rate | 30 | 75 ± 16.4 | 57.1 ± 15.5* | 30 | 72.3 ± 15.4 | 62.6 ± 14.9* |
| Fibrinogen | 60 | 3.69 ± 0.74 | 3.51 ± 0.51 | 30 | 3.82 ± 0.58 | 3.71 ± 0.39 |

*P < 0.05

7. The pharmaceutical composition of Ginkgo biloba extract described in this invention is effective in improving exercise tolerance and extending duration of walking, interval between exercise initiation and angina occurrence and interval between exercise initiation and a 1 mm. decrease of ST segment. Its effectiveness is better than that of the control drug.

TABLE 12

Effects of the Pharmaceutical Composition of
Ginkgo Biloba Extract on the Motor Ability of Patients

|  | Test (n = 21) | | Control (n = 20) | |
|---|---|---|---|---|
| Item | Pre-med. | Post-med. | Pre-med. | Post-med. |
| Total Exercise Time (Seds) | 405 ± 141 | 550 ± 125**^ | 428 ± 136 | 497 ± 144** |
| Total Exercise Equivalent (Mets) | 7.93 ± 2.25 | 10.23 ± 1.97** | 8.13 ± 2.40 | 9.44 ± 2.20* |
| Exercise Equivalent up to 1 mm ST Decrease (Mets) | 267 ± 94 | 344 ± 120** | 303 ± 114 | 305 ± 130 |
| Interval between Exercise Initiation and 1 mm ST Decrease (Mets) | 5.88 ± 1.40 | 7.09 ± 1.75**^^ | 6.30 ± 2 | 6.31 ± 2.15 |
| Interval between Exercise Initiation and Angina Occurring (Sedc) | 390 ± 138 | 523 ± 119** | 399 ± 131 | 480 ± 132** |
| ST Restoration Time (Sedc) | 574 ± 149 | 585 ± 134 | 608 ± 132 | 595 ± 128 |
| ST Segment Decrease During Peak Exercise | 1.60 ± 0.37 | 1.63 ± 0.45 | 1.56 ± 0.48 | 1.58 ± 0.44 |

*P < 0.05; **P < 0.01 as compared with pre-medication; ^P < 0.05; ^^P < 0.01 as compared with the control 8. The pharmaceutical composition of Ginkgo biloba extract described in this invention can be applied to angina pectoris of various kinds and degrees (Tab. 13 & 14). It does not affect blood pressure or heart rate (Tab 15), nor does it affect hepatic or renal functions (Tab 16).

TABLE 13

Effects of the Pharmaceutical Composition of
Ginkgo Biloba Extract with Angina Pectoris of 3 Grades

| Seriousness of Angina Pectoris | No. | Markedly Effective | Effective | No Effect |
|---|---|---|---|---|
| Low-grade | 55 | 23 | 33 | 1 |
| Mid-grade | 80 | 33 | 46 | 1 |
| High-grade | 18 | 3 | 7 | 8 |

TABLE 14

Effects of the Pharmaceutical Composition of
Ginkgo Biloba Extract on Patients with Angina Pectoris of 3 Types

| Types of Angina Pectoris | No. | Markedly Effective | Effective | No Effect |
|---|---|---|---|---|
| Tiredness-induced | 119 | 48 | 65 | 6 |
| Spontaneous | 25 | 6 | 16 | 3 |
| Mixture | 9 | 5 | 3 | 1 |

TABLE 15

Pre- and Post-medication Results of the
Pharmaceutical Composition of Ginkgo Biloba Extract on Blood
Pressure and Heart Rate of Patients in 3 Groups (X ± SD)

|  | Test/Open | | | Control | | |
|---|---|---|---|---|---|---|
| Item | No. | Pre-med. | Post-med. | No. | Pre-med. | Post-med. |
| SBP (kpa) | 153 | 19.1 ± 2.4 | 18.7 ± 2.1 | 90 | 19.2 ± 2.2 | 19 ± 1.8 |
| DBP (kpa) | 153 | 11.4 ± 1.1 | 11.3 ± 1.1 | 90 | 11.5 ± 1 | 11.4 ± 0.9 |
| HR | 153 | 76.9 ± 8.9 | 75.9 ± 7.5 | 90 | 75.6 ± 6.5 | 76.1 ± 7.4 |

TABLE 16

Influence of the Pharmaceutical Composition of
Ginkgo Biloba Extract on the Hepatic and Renal Functions of Patients

|  | Test | | | Control | | |
|---|---|---|---|---|---|---|
| Item | No. | Pre-med. | Post-med. | No. | Pre-med. | Post-med. |
| SGPT | 123 | 16.8 ± 6.6 | 14.8 ± 6.8 | 60 | 13.6 ± 5.9 | 14.3 ± 6 |
| BUN | 123 | 5.81 ± 2.07 | 5.82 ± 3.08 | 60 | 5.75 ± 1.34 | 5.53 ± 1.09 |
| CR | 153 | 81.8 ± 24.1 | 78.2 ± 20.3 | 90 | 84.7 ± 18.3 | 84 ± 20.4 |

What is claimed is:

1. A method for obtaining a Ginkgo biloba composition comprising the steps of:
   (a) obtaining dried Ginkgo biloba leaves;
   (b) breaking the leaves into small pieces;
   (c) putting the broken leaves through a process of reflux in a solution selected from water, C1 to C3 alkanols, acetone, and a combination thereof under conditions permitting the extraction of flavonoids and lactones to produce an extract and a residue;
   (d) separating the extract from the residue;
   (e) concentrating the separated extract to a density of about 1.2 to about 1.25 at 60°C;

(f) applying the concentrate from step (e) to at least two kinds of resin under conditions permitting binding of flavonoids and lactones;

(g) eluting the bound flavonoids an lactones, thereby producing an extract containing flavonoids and lactones from Ginkgo biloba.

2. The method of claim 1, wherein in step (f), the resins are packaged in columns.

3. The method of claim 1, wherein the resins are porous polymer, silicon gel, Aluminum oxide, polyamide, activated charcoal, cellulose or sephadex.

4. The method of claim 2, wherein the columns are eluted with water, C1 to C3 alkanols, acetone, or ester which is methyl or ethyl ester.

* * * * *